United States Patent [19]

Kern

[11] Patent Number: 4,676,790

[45] Date of Patent: Jun. 30, 1987

[54] METHOD OF MANUFACTURE AND IMPLANTATION OF CORNEAL INLAYS

[76] Inventor: Seymour P. Kern, 22 Timbergate, Irvine, Calif. 92714

[21] Appl. No.: 779,808

[22] Filed: Sep. 25, 1985

[51] Int. Cl.⁴ .................... A61F 2/14; A61F 17/32; A61B 17/36

[52] U.S. Cl. .................................. 623/5; 128/1 R; 128/303.1; 128/305

[58] Field of Search .................. 623/5, 6, 4, 1; 128/1 R, 305, 395, 303.1; 351/160 H

[56] References Cited

U.S. PATENT DOCUMENTS

| | | | |
|---|---|---|---|
| 3,562,820 | 2/1971 | Braun | 623/1 X |
| 4,077,411 | 3/1978 | Ward | 128/305 X |
| 4,346,482 | 8/1982 | Tennant et al. | 128/1 R X |
| 4,461,294 | 7/1984 | Baron | 128/303.1 |
| 4,563,779 | 1/1986 | Kelman | 623/5 |
| 4,581,030 | 4/1986 | Bruns et al. | 623/5 |

OTHER PUBLICATIONS

Corneal Surgery—Advanced Techniques in Optithalmic Microsurgery—vol. Two, by Louis J. Girard (Book) The C. V. Mosby Co., St. Louis, Toronto, London, 1981, p. 171 (FIG. 6–26).

Primary Examiner—Ronald L. Frinks

[57] ABSTRACT

A process for making a corneal inlay and implanting the inlay in the human eye, the latter comprising the steps of preparing a lens blank; shaping the blank by laser milling or the like; preparing a recess in the cornea of the patient, the recess being adapted to receiving the shaped inlay whereby the exterior surface of the inlay lies flush with the Bowman's layer; and bonding the inlay to the recess by suturing, laser welding, gluing or other appropriate means.

3 Claims, 8 Drawing Figures

METHOD OF MANUFACTURE AND IMPLANTATION OF CORNEAL INLAYS

BACKGROUND OF THE INVENTION

1. Field of the Invention

The present invention relates generally to the field of corneal implants and more specifically, to a process for replacing corneal refractive tissue.

2. Prior Art

Blindness and severe vision impairment are often caused by corneal defects. Such defects may for example, result from disease such a bullous keratophy or severe corneal damage such as from accidental intrusion of the eye by a foreign object. In addition, the cornea is sometimes the focus of treatment for the correction of vision defects such as myopia, hyperopia and presbyopia such as by radial keratotomy and keratomeleusus. Radial keratotomy involves a process in which preselected incisions of a precalculated depth, direction and number are made in the cornea to reduce corneal curvature for correction of both myopia and astigmatism. Keratomeleusus involves the carving of frozen cut corneal tissue with a cryolathe. An additional cornea treatment for correcting ophthalmic defects is a process known as epikeratophakia in which precarved and lyophilized corneal tissue is rehydrated and sewn back onto the cornea.

The conventional use of corneal transplants for correcting eye defects suffers from a number of disadvantages. By way of example, there is a shortage of supply of living tissue corneal implants since the corneal tissue is obtained from recently deceased individuals. Most states have legislation which requires permission from the donor prior to his death or from the next of kin of the deceased to make such donated corneal tissue available. In addition, even if the tissue is available in adequate quantities, there is a severe risk of contamination of the tissue during handling and transport. Furthermore, in the event that the donor tissue was diseased, such diseases may be transmitted from the donor to the recipient. Furthermore, there is still a need to freeze the donor tissue in order to cut and shape it to suit the recipient's needs. Finally, there is always the question of ethics of handling tissues of the deceased.

Radial keratotomy is a process which is only suitable for correcting relatively mild cases of myopia and astigmatism. More severe cases of these two afflictions as well as all cases of presbyopia, cannot usually be corrected with radial keratotomy. Keratomeleusus and eipkeratophakia both involve a substantial degree of risk in the handling of a patient's own corneal tissue and reshaping that tissue.

The present invention is designed to reduce or entirely overcome the aforementioned disadvantages of the prior art by providing a process for generating and implanting synthesized corneal-like stromal tissue by the solidification of collagens or collagen-like materials derived from gelatin or other sources.

SUMMARY OF THE INVENTION

The present invention comprises the process for implanting corneal inlays into a patient. The corneal inlays may be synthesized from corneal-like stromal tissue by solidification of collagen or collagen-like material that has been treated with a chemical cross-linking substance making the collagen or collagen-like material stiff enough to be laser milled at room temperatures. The cross-linked collagen or collagen-like material is either cryo or laser lathed into a corneal-like shape having the preselected optical characteristics needed by the patient. The laser leaves a protein condensate along the surface which it cuts. The surface of the patient's cornea is then recessed by means of laser milling so that the surface of the implant will lie flush with Bowman's membrane or layer. The synthetic cornea is then implanted in the laser-produced recess allowing a regrowth of the epithelium cells over the top of the lens implant. The synthetic corneal inlay may be bonded to the recessed portion of the patient's cornea by many available means including suturing, laser welding or the use of a collagen glue. The protein condensate left by laser milling the synthetic corneal tissue promotes or supports regrowth or epithelium cells, stops infection and prevents absorption of antibodies. The synthetic tissue prepared in accordance with the present invention may also be used as an envelope for a lens system or may be made of a high index of refraction material to correct refractive defects.

OBJECTS OF THE INVENTION

It is therefore a principal object of the present invention to remedy the aforementioned deficiencies of the prior art by providing a novel method of implanting a corneal inlay in the human eye for replacing corneal tissue of visually impaired individuals.

It is an additional object of the present invention to provide a method for vision deficiencies, the method comprising the steps of: preparing a lens blank by shaping it as a lens suitable for implanting in the human eye; preparing a recess in the surface of the cornea of the recipient for receiving the shaped corneal tissue; and bonding the corneal inlay to the recess formed in the eye.

BRIEF DESCRIPTION OF THE DRAWINGS

The aforementioned objects and advantages of the present invention as well as additional objects and advantages thereof will be more fully understood hereinafter as a result of a detailed description of a preferred embodiment when taken in conjunction with the following drawings in which:

FIG. 6, comprising

DETAILED DESCRIPTION OF A PREFERRED EMBODIMENT

Figure 1:
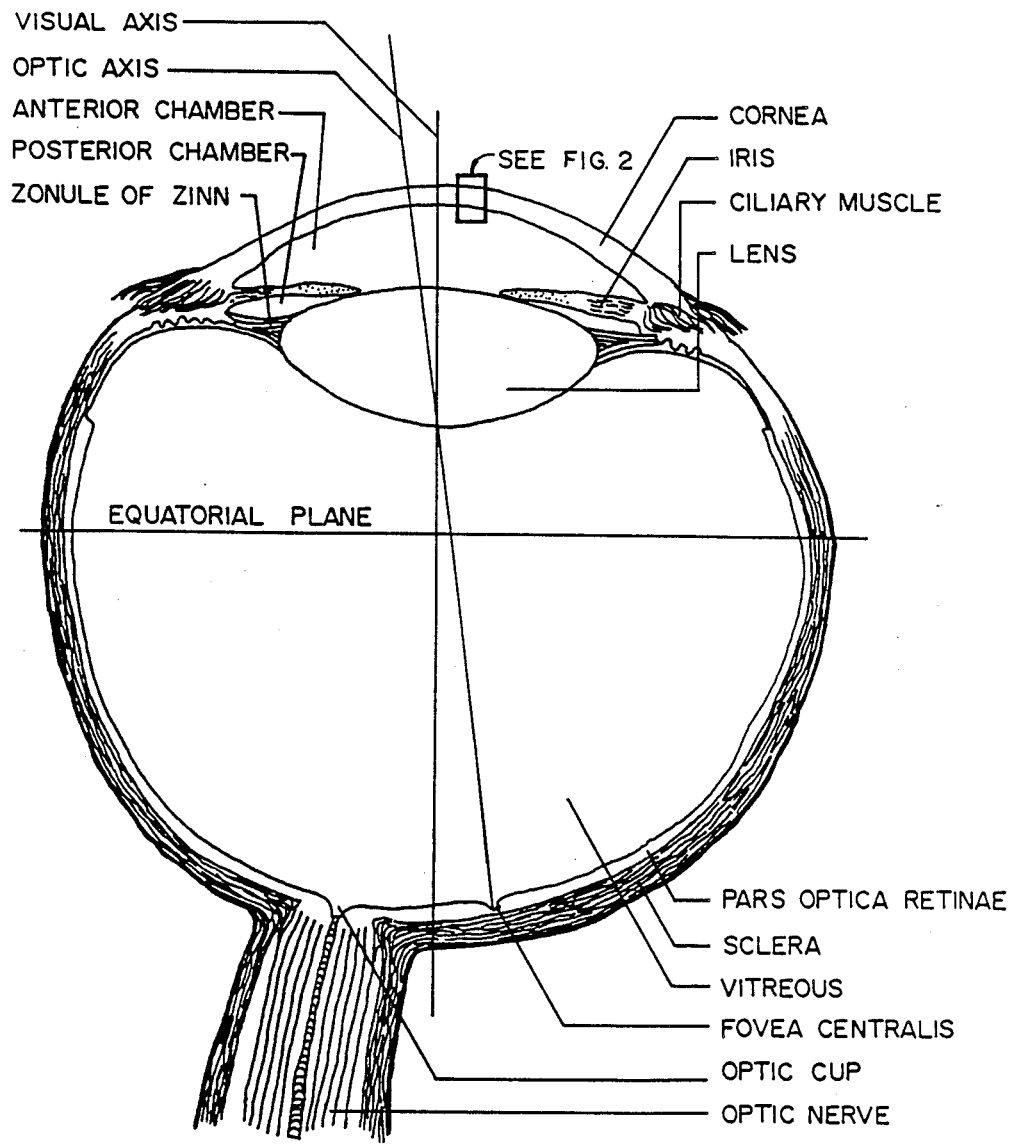
FIG. 1 is a cross-sectional view of the human eye used as an aid in understanding the present invention.
Figure 2:
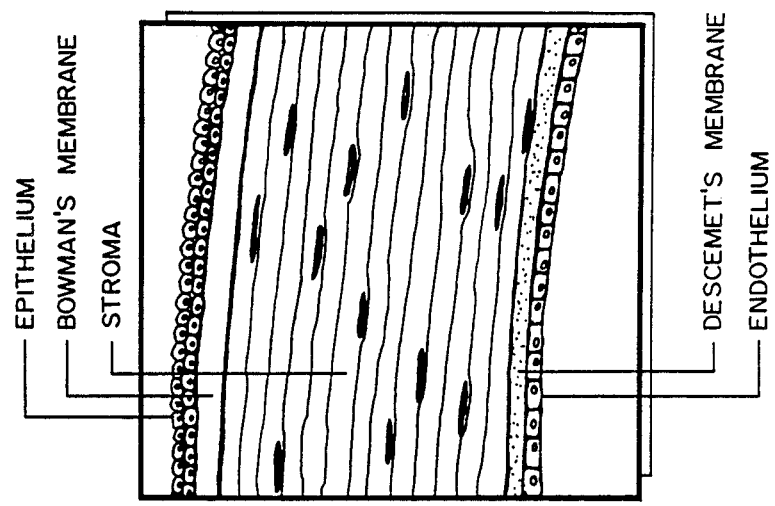
FIG. 2 is an enlarged view of a portion of FIG. 1 illustrating the particular physiology of the eye relevant to the present invention.

FIGS. 1 and 2 are provided herein by way of background material. More specifically, FIGS. 1 and 2 provide physiological descriptions of the human eye and particularly that portion thereof which is relevant to the present invention. As seen in FIG. 1 the cornea of the eye is part of the lens system. Accordingly, if the cornea is defective and as a result of disease or accident does not properly transmit light into the eye, as a minimum vision is at least impaired and in worse cases, blindness may result. Because the cornea is a part of the lens system, the optical characteristics of the eye can be altered by changing the shape and therefore the light bending capacity of the cornea. Thus, altering the surface geometry of the cornea is one way for correcting vision defects such as myopia, presbyopia and astigmatism. In fact, astigmatism is an ophthalmic defect caused by a misshapen cornea. It is for this reason that the prior art processes of radial keratotomy, keratomeleusus and epikeratophakia have been developed. Accordingly, it will be understood that the present invention is advantageous not only for treating unhealthy corneal tissue but is also effective for changing the shape of healthy corneas to correct vision deficiencies which may be the result of other eye defects.

The detailed physiology of the cornea is illustrated in FIG. 2. It will be seen in FIG. 2 that the cornea comprises a series of laminations of different types of stratified tissue. More specifically, the outer layer of the cornea is known as the epithelium which is supported on an inner membrane known as the Bowman's membrane or layer. The inside surface of the cornea, that is, the surface facing the posterior chamber of the eye, is known as the endothelium which is supported on an underlying membrane known as Descemet's membrane. The bulk of the corneal tissue is comprised of striated layers known as the stroma which lies between the Bowman's membrane or layer of the outer surface and the Descemet's membrane of the inner surface. It will be seen hereinafter that in preparing the cornea for receiving the synthetic corneal tissue of the present invention, a laser is used to mill away a portion of the epithelium membrane, Bowman's layer and the stroma to create a recess adapted for receiving a shaped synthetic corneal tissue implant so that the exterior surface of the implant lies flush with the Bowman's membrane layer adjacent the implant. However, reference will first be made to FIG. 3 which illustrates the manner in which such an implant is prepared for bonding into the cornea of the patient.

Figure 3:
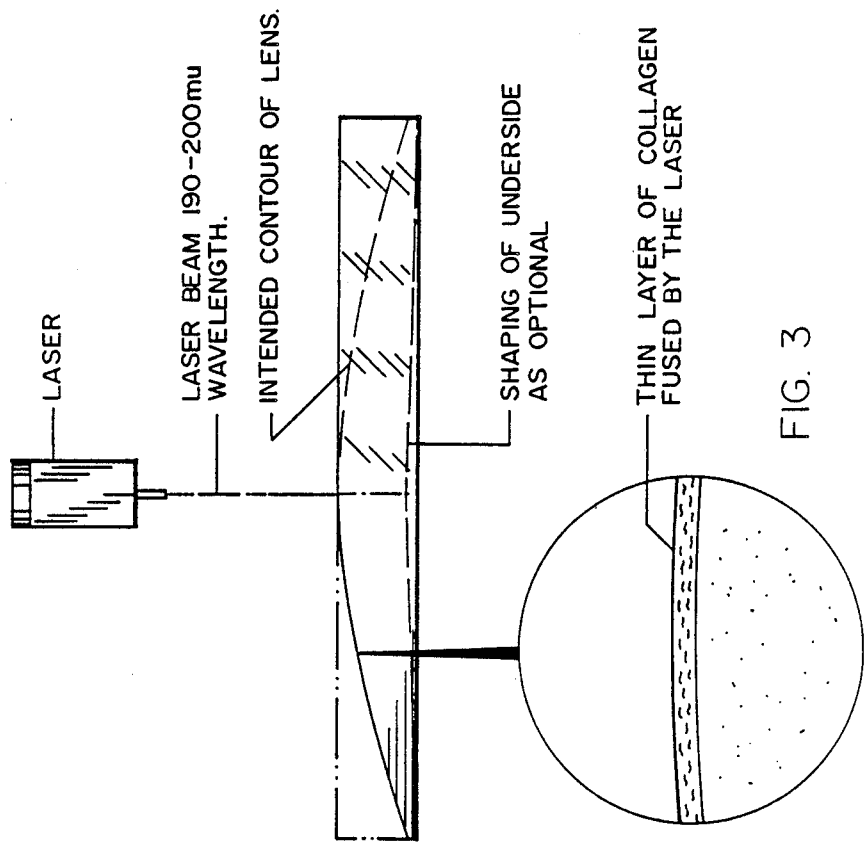
FIG. 3 is an illustration of a portion of the process used for preparing a synthetic corneal implant of the present invention.

More specifically, turning now to FIG. 3 it will be seen that in the particular embodiment illustrated herein a substantially rectangular element of cross-linked collagen or collagen-like material is first prepared. Typically, this element is a substantially flat cross-section of relatively uniform dimensions. A laser having a beam of selected intensity and wavelength is then activated with the beam directed towards the surface of the collagen or collagen-like material thereby milling away a portion of the material for generating the intended contour of the lens as required for an individual patient. Although it is contemplated that the milling of the collagen or collagen-like material will be from one side, so that only one surface of the lens may be contoured, the process of the present invention also contemplates a degree of shaping of the opposite surface of the collagen or collagen-like material if necessary or desirable to produce the required lens characteristics of the synthetic corneal tissue. The synthetic corneal tissue may also be shaped by chemical, biological or radiation techniques to shape the material and leave a protein condensate on its surface.

As noted in FIG. 3, the interaction of the noted laser beam and the cross-linked collagen or collagen-like material produces a thin layer of collagen or collagen-like material that is fused by the laser wherever the milling has taken place. This thin layer comprises a protein condensate which is compatible with eye tissue and will in fact promote or support the growth of adjacent corneal tissue layers as hereinafter described.

Figure 5:
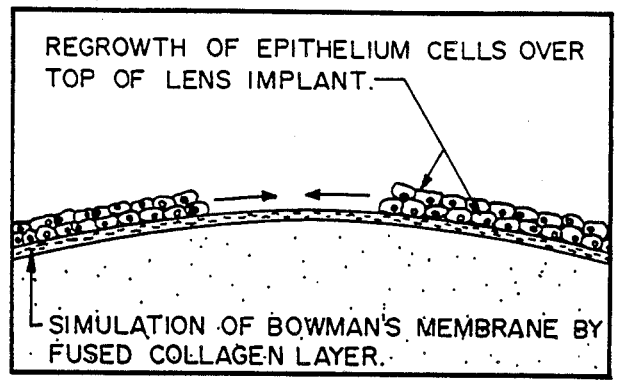
FIG. 5 is an enlarged view of a portion of FIG. 4 showing the corneal regrowth process that secures the implant of the present invention into a human eye.
Figure 4:
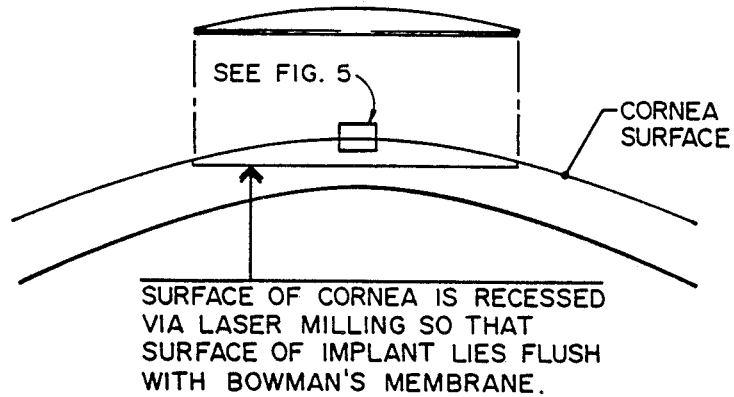
FIG. 4 is an illustration of the manner in which the implant of the present invention is placed in the eye in accordance with the process of the present invention.

As seen in FIGS. 4 and 5, the synthetic corneal tissue contoured by means described in conjunction with FIG. 3 is implanted in a recess of the cornea which is prepared in a similar manner, namely, by laser milling of the patient's corneal tissue. In this manner, a recess is prepared which is adapted to receive a synthetic corneal tissue so that the surface of the implant lies flush with Bowman's membrane or layer. In fact as seen in FIG. 5, the thin layer of collagen or collagen-like material fused by the laser to provide the protein condensate simulates the Bowman's membrane or layer thereby permitting regrowth in the epithelium cells over the top of the lens implant. This regrowth process is illustrated in FIG. 5 where it is seen that the epithelium cells have almost completely covered the synthetic corneal tissue that has been implanted in the patient's eye.

Figure 6C:
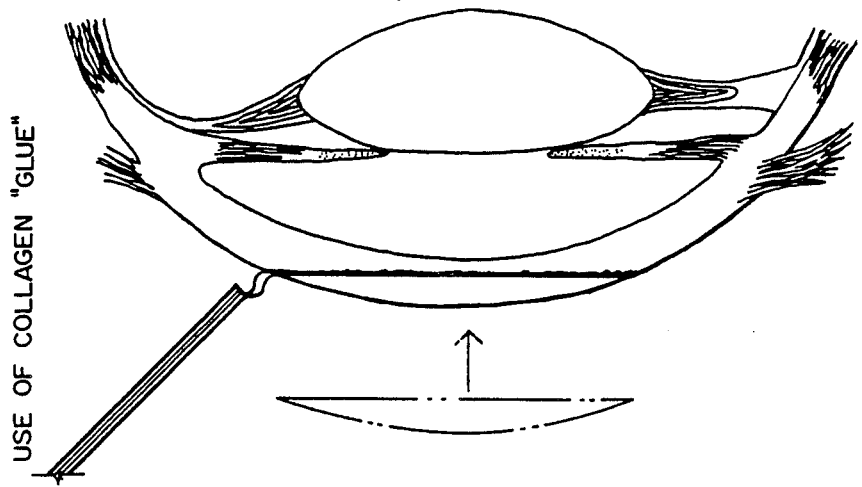
FIGS. 6a, 6b and 6c, illustrates three alternative means for bonding the synthetic corneal tissue of the present invention into a human eye.
Figure 6B:
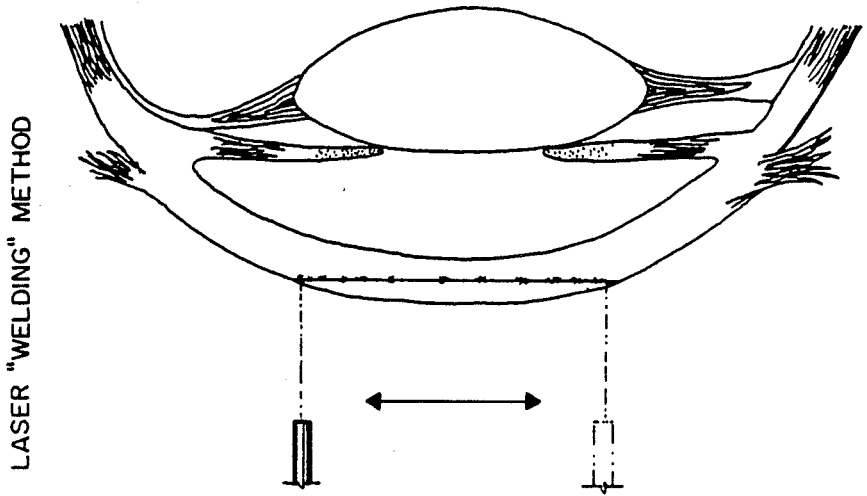
Figure 6A:
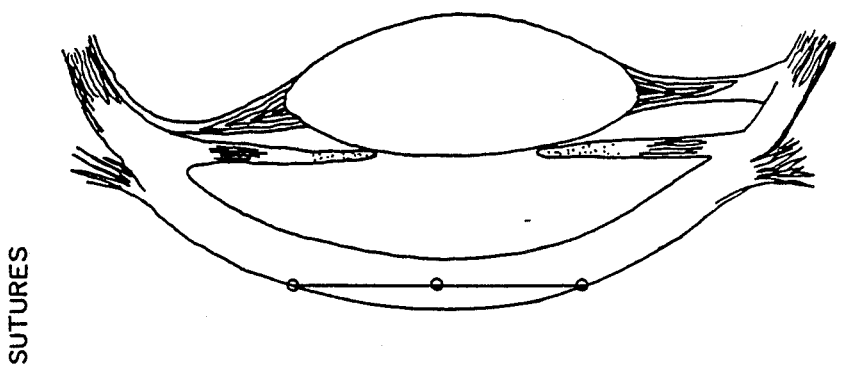

Bonding or the synthetic corneal tissue inlay of the present invention into the remaining portion of the cornea of the patient, may be accomplished by a variety of alternative ways as illustrated in FIG. 6. More specifically, as seen in FIG. 6 which comprises FIGS. 6a, 6b and 6c, the synthetic corneal tissue inlay may be bonded to the recessed cornea of the patient by means of sutures, laser welding or the use of collagen glue. The use of sutures to bond the inlay to the recessed cornea involves the same skills and methods that would be involved in the process of keratomeleusus or epikeratophakia and therefore need not be described herein in any detail. The laser welding method of FIG. 6b involves the use of a carefully controlled laser beam not necessarily different from the milling laser of FIG. 3 to in effect, fuse the tissue between the perimeter of the inlay and the perimeter of the recess thereby securing the inlay within the cornea. The collagen glue bonding method of FIG. 6c involves the use of either cross-linked or uncross-linked collagen or collagen-like material that is still in its liquid phase and is spread on the surface of the recess or the surface of the inlay or both. The glue eventually forms a gel interface that bonds the inlay to the recess of the cornea.

Eventually, regrowth of the epithelium over the top of the lens implant, as well as other natural cell growth that interacts with the protein structure of the collagen or collagen-like material, will secure the synthetic corneal tissue implant in the eye permanently for correcting or restoring the vision of the patient.

It will now be understood that what has been disclosed herein comprises a novel process and article of manufacture, the latter in the form of a synthetic corneal tissue inlay of a gelatin-like collagen or collagen-like material cross-linked to permit laser milling for shaping the material surface whereby to correct or restore the vision of an otherwise defective human eye. The process of the invention involves the steps of preparing a preliminary form of cross-linked collagen or collagen-like material that is transparent to light and then milling the material to give it the desired shape for correcting a particular patient's corneal optical defects. The process includes the further steps of preparing a suitable recess in the corneal tissue of the patient such as by means such as laser milling or conventional slicing so that when the implant is installed in the eye, the surface of the implant lies flush with the Bowman's membrane or layer of the eye. The process is completed with the step of bonding the implant or inlay of synthetic corneal material into the eye by any one of a number of alternative bonding techniques including that of sutures, laser welding or collagen or collagen-like glue.

The aforementioned inlay and process of the present invention overcomes the disadvantages of living tissue corneal implants including the shortage of supply, the contamination of the tissue during handling and transport, the possible transmission of disease to donor to recipient, the need to freeze donor tissue in order to cut and shape it, and the ethics of handling tissues of the deceased. Furthermore, the novel inlay and process of the present invention is deemed to be a unique substitution or adjunct to the prior art processes that are now available for correcting the surface of the cornea to accommodate errors of refraction such as hyperopia, myopia, presbyopia as well as astigmatism caused by asymmetrical corneal shapes. Those having skill in the art to which the present invention pertains will understand that the novel synthetic corneal tissue implants of the present invention need not necessarily be used immediately upon a patient. Blank implants of cross-linked collagen or collagen-like material may be prepared in advance and properly stored for later milling when needed by a patient. Alternatively, a variety of milled synthetic corneal tissue inlays may be prepared to accommodate various ophthalmic needs for future use and stored just as corrective lenses for eyeglasses and contact lenses may now be stored and used upon a patient at a later time. The inlay of the present invention may also be used as a "living" tissue contact lens or as an envelope for a lens system. Furthermore, the optical characteristics of the inlay may be altered by using different refractive index materials as well as by shaping. Various modifications and additions to the invention will now be perceived by those who have had the benefit of the applicant's teaching herein. By way of example, other synthetic materials and other means for shaping the material as well as for preparing the patient's eye for receiving the implant will now occur to those having skill in the art to which the present invention pertains. However, it will be understood that all such modifications and additions are deemed to be within the scope of the invention which is to be limited only by the claims appended hereto.

I claim:

1. A process for replacing a portion of the corneal tissue of the human eye, the process comprising the steps of:
    (a) preparing a lens blank;
    (b) shaping the blank into a desired lens configuration;
    (c) preparing a recess in said eye, said recess being in the corneal tissue and being adapted to receive said shaped blank whereby the outer surface of said blank lies flush with Bowman's membrane; and
    (d) bonding the shaped blank into said recess by laser fusing said shaped blank to said corneal tissue.

2. A process for replacing a portion of the corneal tissue of the human eye, the process comprising the steps of:
    (a) preparing a lens blank;
    (b) shaping the blank into a desired lens configuration by laser milling said blank;
    (c) preparing a recess in said eye, said recess being in the corneal tissue and being adapted to receive said shaped blank whereby the outer surface of said blank lies flush with Bowman's membrane; and
    (d) bonding the shaped blank into said recess.

3. A process for replacing a portion of the corneal tissue of the humam eye, the process comprising the steps of:
    (a) preparing a lens blank;
    (b) shaping the blank into a desired lens configuration;
    (c) preparing a recess in said eye by laser milling said corneal tissue, said recess being in the corneal tissue and being adapted to receive said shaped blank whereby the outer surface of said blank lies flush with Bowman's membrane; and
    (d) bonding the shaped blank into said recess.

* * * * *